United States Patent [19]

Koppel et al.

[11] 4,433,193

[45] Feb. 21, 1984

[54] PROCESS FOR THE PRODUCTION OF ETHANE

[75] Inventors: Paul E. Koppel, Lexington; Joseph J. Williams, Sudbury, both of Mass.; Herman N. Woebcke, Stamford, Conn.

[73] Assignee: Stone & Webster Engineering Corp., Boston, Mass.

[21] Appl. No.: 312,157

[22] Filed: Oct. 16, 1981

[51] Int. Cl.$^3$ .......................... C07C 9/06; C10G 47/22
[52] U.S. Cl. ...................................... 585/752; 208/107
[58] Field of Search .......................... 208/107; 585/752

[56] References Cited

U.S. PATENT DOCUMENTS

| | | | |
|---|---|---|---|
| 2,924,569 | 2/1960 | Souby | 208/107 |
| 3,248,319 | 4/1966 | Bowles et al. | 208/111 |
| 3,309,305 | 3/1967 | Scott | 208/111 |
| 3,363,024 | 1/1968 | Majumdar | 260/683.9 |
| 3,385,782 | 5/1968 | Buss | 208/111 |
| 3,412,010 | 11/1968 | Alpert et al. | 208/112 |
| 3,576,899 | 4/1971 | Ishiguro et al. | 260/676 |
| 3,619,411 | 11/1971 | Wald | 208/108 |
| 3,630,887 | 12/1971 | Mounce et al. | 208/100 |
| 3,842,138 | 10/1974 | Chahvekilian et al. | 208/107 |
| 3,888,761 | 6/1975 | Stewart | 208/112 |
| 4,065,514 | 12/1977 | Bartley et al. | 260/676 |
| 4,115,467 | 10/1978 | Fowler | 260/683 |
| 4,139,452 | 2/1979 | Beuther et al. | 208/107 |

FOREIGN PATENT DOCUMENTS 1265415 3/1972 United Kingdom .
1333776 10/1973 United Kingdom .

Primary Examiner—Delbert E. Gantz
Assistant Examiner—Lance Johnson
Attorney, Agent, or Firm—Hedman, Gibson, Cassella, Gibson & Costigan

[57] ABSTRACT

An improved process for producing ethane from aromatic hydrocarbons is described. Hydrogen and the hydrocarbons are introduced into a catalytically inert reactor zone and are reacted under closely controlled conditions which provide an enhanced yield of ethane.

17 Claims, 1 Drawing Figure

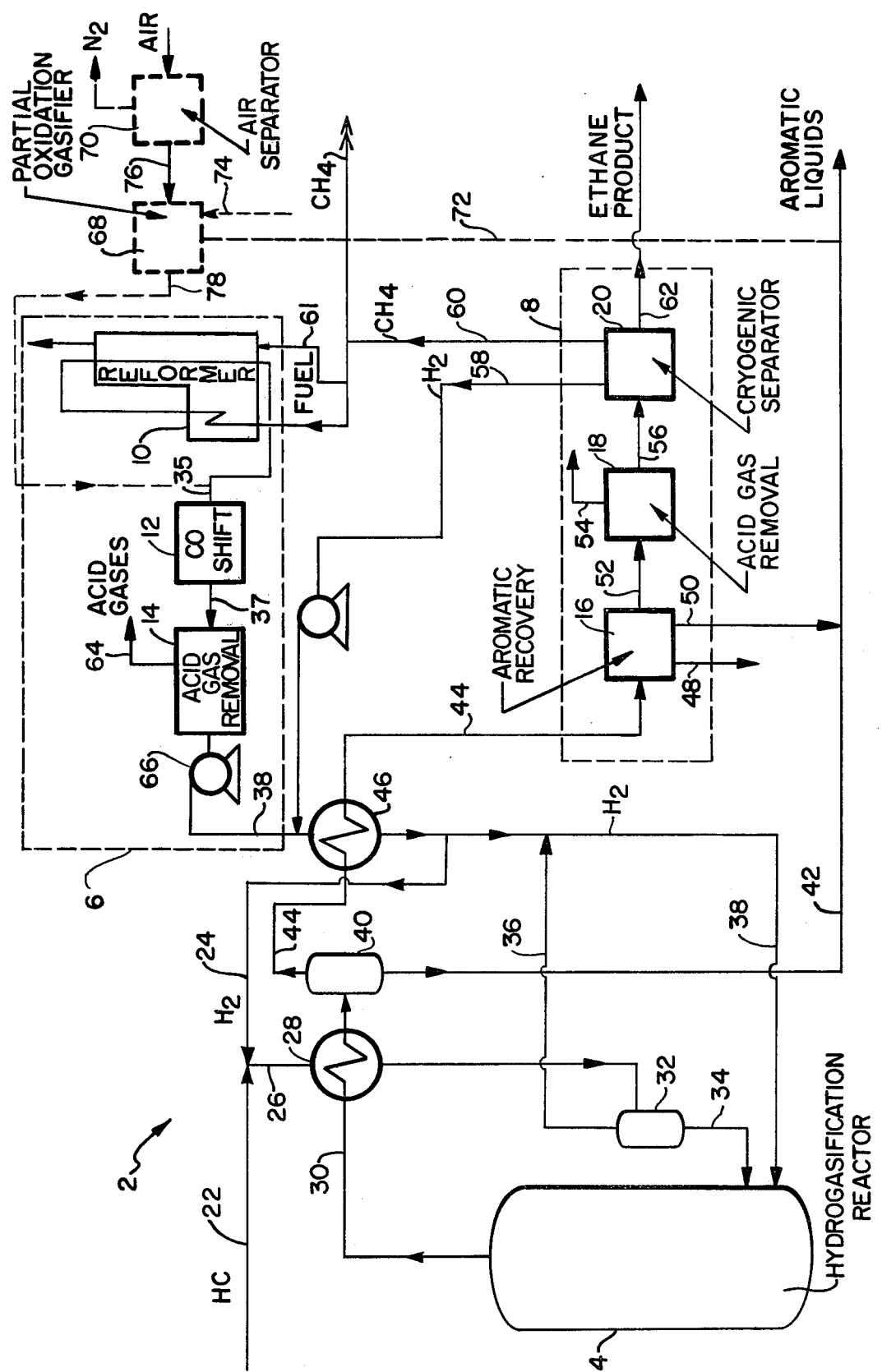

PROCESS FOR THE PRODUCTION OF ETHANE

FIELD OF THE INVENTION

This invention relates generally to the production of lower aliphatic hydrocarbons. More specifically, ethane is produced by hydrogasifying an aromatic feedstock under defined process conditions resulting in high yields of this product, with low levels of coking.

BACKGROUND OF THE INVENTION

The destructive hydrogenation or hydrocracking of hydrocarbons is well-known. In these processes, aliphatic hydrocarbons undergo cracking to produce lower hydrocarbons such as propane, methane, and, especially, ethane. Alkylated aromatic hydrocarbons present undergo dealkylation to at least a minor extent. Non-alkylated aromatic compounds are generally unaffected to any appreciable extent, except under the most severe conditions.

In view of the foregoing, the light hydrocarbon gases of one to four carbon atoms have generally been synthesized as a by-product of such hydrogenation of hydrocracking of aliphatic hydrocarbons. Representative processes involving, for example, Naphtha are described in British Patent Specification Nos. 1,265,415 and 1,333,776. Recommended conditions for these processes include a high hydrocarbon to hydrogen ratio (i.e., the ratio of hydrogen fed to the reactor zone to that which is stoichiometrically required to convert all feedstock carbon to methane) and temperatures of about 1100°–1400° F. These conditions are designed to maximize production of ethane, which may then be converted to ethylene.

Hydrogasification of predominantly aliphatic liquid feedstock to produce ethane for subsequent steam cracking results in increased yields of ethylene, (as compared to directly steam cracking the feedstock), but at the expense of other valuable cracking co-products, such as propylene and butadiene. Although petroleum distillate, crude petroleum and heavy oils are claimed to be suitable feedstocks for the process described in British Patent Specification No. 1,265,415, that process is, in practice, limited to naphtha feedstock. With heavier feedstocks, coking is increased beyond that tolerable of many reactor types. While high yields of ethylene can be obtained by the hydrogasification of naphtha followed by steam cracking of the ethane product, naphtha can be directly steam cracked to yield comparable total $C_2$–$C_4$ petrochemical products (ethylene, propylene and butadiene).

A method of processing these heavy aliphatic hydrocarbon feedstocks which has been the subject of numerous patents, contemplates the use of particulate catalyst beds, referred to in the art as "ebullated beds". Examples of such patents are U.S. Pat. Nos. 3,630,887; 3,248,319; 3,363,024; 3,412,010; 3,888,761; 3,576,899; 4,065,514; and 3,385,782. Use of these catalyst particles, according to U.S. Pat. No. 3,309,305, is desirable in order to accomplish effective contact between fluids and particles.

The prior art, such as U.S. Pat. No. 3,619,411 issued to Shell Oil Company, teaches that effective hydrogenation of heavy high-boiling hydrocarbons requires the presence of a catalyst in order to prevent unsaturated fragments from condensing to form coke. The disadvantages of heavy feedstock processes include the identification and addition of a catalyst that will survive the often severe and highly coking reaction conditions. The need for removal of the catalyst from the effluent stream is also a drawback.

Thus, the light paraffinic hydrocarbon gases, i.e., methane through butane, have generally been synthesized at relatively low yields through the catalytic cracking and hydrogenerating of aliphatic hydrocarbons. Because the primary processing value of certain of these gases, specifically ethane, is for the production of ethylene, use of predominantly aliphatic hydrocarbon feedstocks has until now been necessary in order to maximize ethylene yields. This maximization occurs at the expense of valuable co-products of gas oil steam cracking such as propylene and butadiene.

Because of the increasing demand for light hydrocarbon gases, it would be valuable to have a process for producing light gases in higher yields than have generally been obtainable. Light hydrocarbon gases of one to four carbon atoms are generally produced from petroleum at the expense of gasoline. It would be particularly valuable to have a method of processing high boiling feeds, particularly aromatic feedstocks, directly to light hydrocarbon gases as a principal reaction product. These are more difficult to refine and less valuable for gasoline production.

It is also desirable to develop a process that would not only provide high yields of light aliphatic gases, but which would neither require the presence of a catalyst nor consume valuable liquid steam cracking feedstocks, such as naphtha and petroleum gas oils. Such a process could only evolve where the amount of coking was significantly reduced and where ethylene via ethane could be derived from an otherwise low value feedstock.

In an attempt to arrive at such a process, U.S. Pat. No. 4,115,467 issued to Fowler teaches the production of a $C_2$ hydrocarbon from higher hydrocarbon feeds by hydrogenation in a fluidized bed. This bed may, but need not, contain catalyst. The temperature is maintained above the threshold temperature for the reaction by supplying hot combustion gases to the hydrogenation zone, making the subject process less energy efficient.

In an unrelated process, U.S. Pat. No. 4,139,452 describes the hydrogenation of coal liquids and fluid catalytic cracker liquids. This process results in some by-product ethane; however, it is primarily directed to the production of benzene.

SUMMARY OF THE INVENTION

It has been determined that light hydrocarbon gases, specifically ethane, may be produced from highly aromatic feedstocks by hydrogasification without need of a catalyst under certain reaction conditions. The current invention includes processing a feedstock of aromatic hydrocarbons and hydrogen at a predetermined ratio in a reactor maintained under controlled operating conditions of temperature, pressure and residence time to yield ethane.

The feedstock of the present invention may include substantially any fluid hydrocarbon. This method is designed to hydrogasify heavy highly aromatic feedstocks containing hydrocarbons including, but not limited to gas oils, coal-derived liquids, residual stock e.g., petroleum resids, cyclic stocks, topped crudes, reduced crudes, high boiling hydrocarbon fractions derived from tars, pitches, asphalts, shale oil, bitumen etc., fluid catalytic cracking oils such as FCC Furnace Oils and FCC Decanted Oils and the like. By "FCC Furnace Oils", it is meant to include product from a conventional fluid catalytic cracking process having a boiling range at ambient pressure of about 428° F. to about 653° F.; by "FCC Decanted Oils", product from a conventional fluid catalytic cracking process having a boiling range of about 653° F. to about 950° F.

An attribute of this invention is the ability to obtain ethane from ring carbons of aromatics. Consequently, feedstocks containing non-alkylated aromatics represent a preferred aspect of the present invention.

A hydrogen rich gas must also be fed to the hydrogasifier. This hydrogen reacts with the hydrocarbon feedstock to produce predominantly methane, ethane and a benzene rich liquid; the object of this invention being to maximize the yield of ethane. Hydrogen may be supplied by any conventional process such as steam reforming or partial oxidation or by the use of hydrogen rich refinery off-gases.

The hydrogenating gas may be a gaseous mixture consisting mainly, and preferably essentially, of hydrogen (measured by volume). Hydrogen can be produced from synthesis gas, which is a mixture of hydrogen and carbon monoxide obtained by the reaction of carbonaceous materials, for example, coal, coke or hydrocarbons, with steam and/or oxygen. An admixture so obtained may be converted into a gas consisting essentially of hydrogen by reaction with steam, in accordance with the well-known water gas shift reaction, followed by bulk removal of the carbon dioxide.

The presence of certain other components in the hydrogen rich gas may be desirable. Most notably, it has also been determined that where large quantities of methane are present in the feedstock, the ethane yields are further enchanced.

In all instances, the hydrogen ratio in the feedstock—i.e., the ratio of actual hydrogen to that which would be stoichiometrically required to convert all feedstock carbon to methane—should be maintained above about 0.5 and preferably between 1 and 4. Ethane yield has been found to increase with increasing hydrogen ratio. However, a ratio in excess of about 4 produces no substantial improvement.

The reaction between hydrocarbon feedstock and hydrogen may be carried out in any suitable reactor. For example, a fixed bed, fluidized bed, gas recycle, or solids entrained reactor may be employed, the choice of reactor being dependent upon the desired temperature profile, residence time and feedstock characteristics. For example, fluidized bed and gas recycle reactors may be employed to maintain a temperature profile approaching, if not in fact, isothermal. Solids entrained reactors on the other hand are more appropriately employed where short residence times—i.e., less than one (1) second—are desired. Preferably, the reaction is conducted in a non-catalytic fluidized bed of inert material such as silica-alumina, bauxite, sand, zircon, quartz, magnesia, alumina, magnesia-alumia, etc.

The reaction conditions needed to achieve high ethane yields and optimum selectivity of ethane must be carefully controlled. The average temperature in the reaction zone should be maintained at between about 1100° F. and about 1600° F., preferably within the range of about 1200° F. to about 1500° F. The total pressure in the reaction zone should be in the range of about 300 to about 2500 psia, with 500 psia to 2000 psia being preferred. Lastly, the residence time of the reactants in the reactor should be less than about 240 seconds and desirably less than 30 seconds. For enhanced selectivity (weight ratio of ethane to methane produced) in the yield, less than 3 seconds, or even one second residence time is desirable.

Maintaining the reaction conditions within these prescribed ranges is important. In particular, it has been discovered that the selectivity of ethane to methane decreases with increasing temperature and that, for given operating conditions, ethane selectivity may be further improved by operating as nearly isothermal as possible. Moreover, this may be accomplished while simultaneously minimizing the production of coke.

In view of these discoveries, the feedstock is desirably preheated, before reaction. This may be accomplished by mixing the hydrocarbon and hydrogen, and subsequently preheating the mixture. However, in some cases it is desirable to preheat the hydrocarbon and hydrogen separately to the same or different temperatures and to mix them together before or upon introduction to the reactor.

In all cases, the hydrocarbon and hydrogen are so preheated that the composite hydrogen and hydrocarbon "mixed preheat temperature" (that is to say, the temperature of the preheated mixture or the temperature after the reactants have been mixed together) is below the reaction temperature, but is high enough to maintain the desired reaction temperature during the residence time within the reactor zone. Depending upon the heat of reaction, the extent to which the reaction proceeds, the effectiveness of the thermal insulation of the reactor, and the internal dimensions of the reactor, the mixed preheat temperature may vary substantially.

A minimum mixed preheat temperature of 1100° F., is preferred. A higher temperature of up to that at which the reactor zone is to be maintained is preferable because it allows for a more nearly isothermal operation. A variation of temperature of less than 50, preferably less than 20, Fahrenheit degrees throughout the reactor zone is desired.

By following the above parameters, it has been found that a yield of ethane of at least 20 weight percent, based on hydrocarbon feed may be obtained. In general, the ethane yield ranges from about 25 to about 60 weight percent, while coking is maintained below 5, generally below 3, percent by weight of feedstock.

DESCRIPTION OF THE DRAWING

The drawing is a schematic of the process of the invention.

BRIEF DESCRIPTION OF THE PREFERRED EMBODIMENT

The process of of the present invention is directed to the production of high yields of ethane. Aromatic hydrocarbon feedstocks are subjected to hydrogasification, without the need of a catalyst and under conditions at or approaching isothermal.

The quantity of hydrogen present, relative to hydrocarbon feedstock, is at least sufficient to convert a major portion of the aromatic content of the feedstock to saturated hydrocarbon gases. With all other operating variables constant, an increase in the hydrocarbon ratio increases the conversion of hydrocarbon feedstock to gaseous product, increases the ratio of ethane to methane yield rates, and decreases the rate of coking.

An important feature of the present invention lies in both the feedstock employed and in the manner in which the reaction is carried out. In accordance with this invention, ethane production is maximized with an accompanying and unexpected decrease in in coking. Moreover, this is accomplished without the need of a catalyst.

The feedstock preferably has an aromaticity of at least 40, most preferably 50 to 80 percent. It may be, for example, a coal-derived liquid.

Still further advantages are obtained by feeding large quantities of methane along with the hydrogen in the hydrogenating gas, for example, amounts ranging in the order of about 25 molar percent to about 75 molar percent based upon the total amount of hydrogen. This added methane has a beneficial effect on the equilibrium of the reaction and increases selectivity by lessening the kinetic driving forces that act to crack the produced ethane to methane.

The process that achieves the objects of the invention is initiated by delivering coal liquid/hydrogen feed to the bottom of a reactor maintained at 1500 psia and 1400° F. The reactor is preferably a fluidized bed of silica alumina particles having a particle size of under 100 microns. The reaction products exit the top of the reactor and are quenched immediately by cooling.

All heat necessary for the hydrogenating reaction is supplied by the hydrocarbon/hydrogen preheat(s) plus the resulting exothermic heat of reaction. A further objective of the preferred embodiment is to carry out the reaction at nearly isothermal conditions. The use of a fluidized bed type reactor facilitates the above objectives. Should the exothermic heat of reaction vary, causing a temperature change in the fluidized bed, an auxiliary control may be required to maintain conditions. Auxiliary control in such an instance may be achieved by adding (or removing) solid bed material which are of a temperature to compensate for these variations.

The product effluent from the reactor may be treated for recovery of ethane by conventional methods. Thus, for example, the reaction products can be fed to a cooler in which any readily condensible components are separated from the product stream while the gaseous products pass on for further treatment. Such readily condensible products typically comprise aromatic liquid hydrocarbons and water.

After cooling, the gaseous effluent may be washed. An oil is normally used to wash the last traces of aromatic liquid hydrocarbon from the gaseous products. The oil may then be passed to a stripper for recovery of the aromatic liquid hydrocarbon, before being recycled to the washing stage.

After removal of any aromatic hydrocarbon and water from the product effluent, the product effluent will usually consist of methane, ethane, and minor amounts of propane, ethylene and other gaseous hydrocarbons, carbon oxides and unreacted hydrogen. This gaseous product mixture can be further processed by methods well known in the art. Generally this involves a step-wise cryogenic separation.

An illustration of a system 2 in which the process for maximizing ethane from the hydrogasification of aromatic hydrocarbon can be performed is shown in the drawing.

The system 2 includes a hydrogasification reactor 4, a hydrogen make-up system 6 and a product separation system 8.

The hydrogen make-up system 6 includes a methane reformer 10, a carbon monoxide shift reactor 12, and a carbon dioxide removal system 14.

The product separation system 8 is comprised of an aromatic recovery system 16, an acid gas removal system 18 and a cryogenic separation system 20.

In the process, highly aromatic hydrocarbons, such as coal liquids, pyrolysis fuel oils, fluid catalytic cracked oils, and coal gasification tars, are fed through line 22 and mixed with hydrogen from line 24. The hydrocarbon-hydrogen mixture is introduced through line 26 into the cold side of a heat exchanger 28. The overhead from the hydrogasification reactor passes directly, via line 30, through the hot side of the heat exchanger 28.

The heated hydrocarbon and hydrogen mixture is delivered to a liquid vapor separator 32. Therein the liquid is separated from the vapor and passed through line 34 to the hydrogasification reactor 4. The vapor passes overhead through line 36 and mixes with recycled hydrogen which is being delivered to the hydrogasification reactor 4 through the hydrogen line 38.

The hydrogasification reactor 4 is maintained at essentially an isothermal condition in the range of 1100° to 1600° F. and relies principally on the exothermic heat of reaction and feed pre-heat to provide the necessary heat. Conventional means are used to regulate the hydrogasification reactor 4 at an isothermal condition.

The quenched product from the hot side of the heat exchanger 28 continues into a liquid vapor separator 40. The heavier bottoms from the separator 40 is passed through line 42 and processed with other polyaromatics produced in the system. The overhead passes through line 44 which passes through the hot side of a heat exchanger 46 and on to the product separation system 8. The overhead from line 44 is first passed through the aromatic recovery system 16 wherein the $C_6+$ product is separated from the gaseous product. The monoaromatics such as BTX are passed through line 48 and the polyaromatics through line 50 to be joined with the polyaromatics in line 42. The unreacted hydrogen and other gaseous product from the aromatic recovery system are passed through line 52 to the acid gas removal system 18 wherein $H_2S$, $NH_3$ and $H_2O$ are separated and discharged through line 54. The remaining gaseous product is sent through line 56 to the cryogenic separating system 20. Therein high purity hydrogen is removed and sent through line 58 directly to the hydrogen delivery line 38. Methane separated in the cryogenic separating system 20 is sent through line 60 to the hydrogen make-up system 6. The product ethane is sent out through line 62.

Make-up hydrogen is produced in a conventional manner in a methane fired steam-methane reformer 10 to which the methane from the cryogenic separating system 20 is delivered as both feed and fuel through lines 60 and 61 respectively. Higher efficiency advanced concepts, such as power reforming, can also be utilized. The product from the steam-methane reformer 10 is delivered to the carbon monoxide shift reactor 12 through line 35, and thereafter to the acid gas removal system 14 through line 37, wherein the carbon dioxide and other impurities from the hydrogen are removed through line 64. The hydrogen is elevated in pressure in a compressor 66 and then delivered through the cold side of the heat exchanger 46 wherein it is pre-heated. The pre-heated hydrogen is delivered directly to the hydrogasification reactor 4 via line 38 and is also mixed via line 24 with the hydrocarbon feed for delivery to the hydrogasification reactor 4 via exchanger 28.

The system also includes alternative means to generate hydrogen. A partial oxidation gasifier 68 and an air separation plant 70 are provided to produce hydrogen (via synthesis gas) from the partial oxidation of a portion of the polyaromatics from line 42. Line 72 is shown as an alternative to deliver the polyaromatics to the partial oxidation gasifier 68. The partial oxidation gasifier 68 reacts liquid hydrocarbon from line 72 with steam delivered from line 74 and oxygen from the air separation plant 70. The hydrogen generated in the partial oxidation gasifier 68 is provided with a line 78 that can be used optionally to deliver the synthesis gas to the hydrogen purification system associated with the steam methane reformer.

The present invention may be more fully understood by reference to the following examples which are to be construed as illustrative but not limiting the scope of the present invention.

EXAMPLE 1

A coal liquid boiling above 400° F. is fed to a stirrer-assisted fluidized bed reactor at a rate of 0.92 pounds per hour along with 0.465 pounds per hour of pure hydrogen. The average reactor zone temperature is 1351° F., with the reactor being isothermal to within 10° F. Other operating conditions include a pressure of 1500 psia, a hydrogen ratio of 2.25 and a residence time of 126 seconds.

The percent yield from hydrogenation (based on weight of coal liquid) is 59 percent methane, 29 percent ethane, 23 percent aromatic liquid and 4 percent coke.

EXAMPLE 2

Pyrolysis fuel oil, derived as a by-product of steam cracking gas oil, is fed to a fluidized bed reactor at a rate of 0.91 pounds per hour along with 0.904 pounds per hour of hydrogen. The average reactor zone temperature is 1386° F., with the maximum being 1490° F. Other operating conditions include a pressure of 1500 psia, a hydrogen ratio of 4.2, and a residence time of 61 seconds.

The percent yield from hydrogenation (based on weight of fuel oil) is 23 percent methane, 25 percent ethane, 55 percent aromatic liquids and 4 percent coke.

EXAMPLE 3

Fluid catalytic cracking furnace oil at a rate of 0.091 pounds per hour and hydrogen at a rate of 0.0638 pounds per hour is fed to a packed bed reactor. The bed is composed of −10 to +20 mesh quartz chips. The average reactor zone temperature is 1425° F. and maximum reactor temperature is 1549° F. Other reaction conditions include a pressure of 600 psia, hydrogen ratio of 3.0, and a residence time of one second.

The percent yield from the above hydrogenation is 35 percent methane, 22 percent ethane, 51 percent aromatic liquids liquids and one percent coke.

EXAMPLE 4

Chemical grade naphthalene ($C_{10}H_8$) is fed at a rate of 1.85 pounds per hour and hydrogen at a rate of 0.466 pounds per hour to a stirrer-assisted fluidized bed reactor. The average reaction zone temperature is 1360° F. with the reactor being maintained within 10° F. of isothermal. Other reaction conditions include a pressure of 1500 psia, a hydrogen ratio of 1.9 and a residence time of 82 seconds.

Products of the reaction are 44 percent methane, 25 percent ethane, 41 percent aromatic liquids and three percent coke.

EXAMPLE 5

The process of Example 3 is repeated utilizing a pressure of 1500 psia. The feedstock is passed through the reactor zone at varying rates to determine the affect of residence times on selectivity for ethane over methane production. The results are as follows:

| Residence time | Selectivity (ethane/methane by weight) |
|---|---|
| 25 Seconds | 0.1 |
| 15 Seconds | 0.3 |
| 5 Seconds | 0.4 |
| 3 Seconds | 0.5 |
| 2 Seconds | 0.6 |

These results show the markedly increasing selectivity of ethane production encountered at shorter residence times in accordance with the process.

It is to be understood that changes may be made in the particular embodiments of the invention described which are within the full intended scope of the invention as defined by the appended claims.

We claim:
1. A process for the production of ethane comprising:
   (a) introducing a feedstock comprising mainly aromatic hydrocarbons and hydrogen into a non-catalytic reactor zone, the amount of hydrogen being between 1 and 4 times the stoichiometric requirement to convert all carbon in said feedstock into methane;
   (b) reacting said feedstock at a temperature between 1100° and 1600° F. and pressure between 300 and 2500 psia for less than 240 seconds;
   (c) discharging the resultant ethane-containing reaction product from said zone; and
   (d) immediately cooling said product.
2. The process of claim 1, wherein the reactor zone comprises a fluidized bed of inert solids.
3. The process of claim 1, wherein the feedstock hydrocarbons are at least 40 mole percent aromatic.
4. The process of claim 1 comprising the further step of adding methane to the hydrogen.
5. The process of claim 1 comprising the further step of adding methane to the hydrogen in the hydrogenating gas in amounts in the order of about 25 molar percent to about 75 molar percent based on the total amount of hydrogen.
6. The process of claim 1, wherein the reaction zone is essentially isothermal.
7. The process of claim 1, wherein the feedstock in the reaction zone is heated essentially exclusively through heat of reaction of said feedstock.
8. The process of claim 1, wherein the residence time is less than about 3 seconds.
9. The process of claim 1, wherein the temperature in the reaction zone is between 1200° and 1500° F.
10. The process of claim 1, wherein the pressure in the reaction zone is between 500 to 2000 psia.
11. The process of claim 1, wherein the residence time in the reaction zone is less than 1 second.

12. The process of claim 1, wherein the aromatic hydrocarbon is preheated to a temperature of at least 1100° F. before introduction to the reactor zone.

13. The process of claim 12 wherein the hydrogen is preheated to at least 1100° F. before introduction to the reactor zone.

14. The process of claim 13, wherein the hydrogen is admixed with the aromatic hydrocarbon in the reactor zone.

15. The process of claim 1, wherein the feedstock hydrocarbon comprises non-alkylated aromatics.

16. The process of claim 1 comprising the further step of producing a portion of the hydrogen from methane produced in the hydrogasification reaction.

17. The process of claim 1 further comprising the step of producing a portion of the hydrogen from the polyaromatics produced in the hydrogasification reaction.

* * * * *

UNITED STATES PATENT AND TRADEMARK OFFICE
CERTIFICATE OF CORRECTION

PATENT NO. : 4,433,193

DATED : February 21, 1984

INVENTOR(S) : Paul E. Koppel; Joseph J. Williams and Herman N. Woebcke

It is certified that error appears in the above—identified patent and that said Letters Patent is hereby corrected as shown below:

Column 4, line 65, change "hydrocarbon" to --hydrogen--.

Signed and Sealed this

Nineteenth Day of June 1984

[SEAL]

Attest:

GERALD J. MOSSINGHOFF

Attesting Officer

Commissioner of Patents and Trademarks